United States Patent [19]

Hayashi et al.

[11] Patent Number: 5,066,657
[45] Date of Patent: Nov. 19, 1991

[54] CROTONIC ACID AMIDE DERIVATIVES AND INSECTIDES CONTAINING THE SAME

[75] Inventors: Shunji Hayashi; Satoshi Yamanaka; Sayoko Kawaguchi; Teruhiko Ishii; Toshiya Kimata; Naoaki Misu, all of Tokyo, Japan

[73] Assignee: SDS Biotech K.K., Tokyo, Japan

[21] Appl. No.: 520,411

[22] Filed: May 8, 1990

[30] Foreign Application Priority Data

May 9, 1989 [JP] Japan .................. 1-114090

[51] Int. Cl.$^5$ ................ A61K 31/275; A61K 31/495; C07D 239/02; C07C 255/50
[52] U.S. Cl. .................. 514/269; 514/332; 514/333; 514/341; 514/346; 514/406; 514/521; 514/465; 544/333; 544/334; 544/335; 546/256; 546/265; 546/279; 546/291; 548/375; 548/378; 549/438; 549/439; 558/393
[58] Field of Search ............ 544/333, 334, 335; 546/256, 265, 291, 279; 548/378, 375, 376; 549/438, 439; 558/393; 514/269, 332, 333, 341, 346, 406, 521, 465

[56] References Cited

U.S. PATENT DOCUMENTS 4,515,731 5/1985 Bachman et al. ............ 558/393

FOREIGN PATENT DOCUMENTS 0088545 9/1983 European Pat. Off. .
1067427 10/1957 Fed. Rep. of Germany .

OTHER PUBLICATIONS

PCT/AU84/00145, Huppatz et al., published Feb. 14, 1985.

Primary Examiner—Johann Richter
Attorney, Agent, or Firm—Sughrue, Mion, Zinn, Macpeak & Seas

[57] ABSTRACT

A crotonic acid amide derivative represented by formula (I):

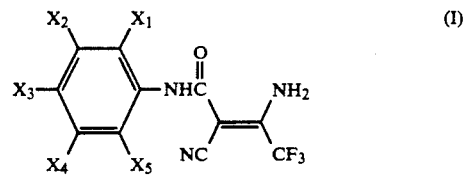

wherein $X_1$, $X_2$, $X_3$, $X_4$, and $X_5$, which may be the same or different, each represents a hydrogen atom, a halogen atom, a substituted or unsubstituted lower alkyl group, a substituted or unsubstituted lower alkyl group, a lower haloalkyl group, a lower haloalkoxy group, a nitro group, a substituted or unsubstituted lower alkanesulfonyl group, a substituted or unsubstituted alkanesulfonyloxy group, a substituted or unsubstituted benzenesulfonyl group, a substituted or unsubstituted benzenesulfonyloxy group, a substituted or unsubstituted phenoxy group, a substituted or unsubstituted benzyloxy group, a dialkylamino group, a mono- or di-lower alkanesulfonylamino group, a substituted or unsubstituted lower alkythio group, a $-SO_2R_1$ wherein $R_1$ represents a lower alkyl group or a lower haloalkyl group, a lower alkoxycarbonyloxy group, a substituted or unsubstituted alkoxycarbonyl group, a $-CH=N-OR_2$ group wherein $R_2$ represents a lower alkyl group, a substituted or unsubstituted pyrazolyl-1-yl group, a substituted or unsubstituted pyridyloxy group, or a pyrimidyl group; $X_2$ may be bonded to $X_1$ or $X_3$ to form a ring, and an insectide containing the same. The compound of formula (I) has broad insecticidal activity against notixious insects, particularly Diptera and Lepidoptera.

5 Claims, No Drawings

CROTONIC ACID AMIDE DERIVATIVES AND INSECTIDES CONTAINING THE SAME

FIELD OF THE INVENTION

This invention relates to a novel crotonic acid amide derivative, and an agricultural and horticultural insecticide or an insecticide for the prevention of infectious diseases which contains the crotonic acid amide derivative. More particularly, it relates to a crotonic acid amide derivative represented by formula (I) shown below and an insecticide containing as an active ingredient the same having insecticidal activities on noxious insects, such as Lepidoptera and Diptera.

BACKGROUND OF THE INVENTION

A number of insecticides have hitherto been developed and used for the purposes of increasing production of foodstuffs, securing foodstuffs, and preventing infectious diseases mediated by insects. It is a well-known fact that these insecticides have been of wide application for agricultural and horticultural use or for the prevention of infectious diseases, and remarkable results have been accomplished.

On the other hand, however, resistance of insects to the conventional insecticides which leads to reduction of insecticidal activity has been developed, giving rise to a world-wide problem, and there has been therefore a keen demand to discover a novel insecticide.

In more detail, insects having resistance to chemicals, such as chlorinated organic compounds, organophosphorus compounds, carbamate compounds, pyrethroid compounds, and skin-formation inhibitory agents, have come forth, and these resistant insects hard to control tend to increase. It is thus assumed that the problem will be more complicated from now on, making control more difficult.

Accordingly, insecticides to be developed hereinafter are required to have no cross resistance with the above-described conventional insecticides and, as a matter of course, exhibit strong insecticidal activity against noxious insects which have not yet developed resistance. To this effect, it is essential to develop an insecticide having an entirely new chemical structure.

SUMMARY OF THE INVENTION

In order to solve the problems set forth above, the inventors have now synthesized crotonic acid amide derivatives whose chemical skeleton is quite unique and entirely different from the chemical structures of the known insecticides and found that these derivatives have insecticidal activity against noxious insects, such as Lepidoptera and Diptera, thus having reached the present invention.

The present invention provides a crotonic acid amide derivative represented by formula (I) shown below and an insecticide containing the crotonic acid amide derivative represented by formula (I) as an active ingredient.

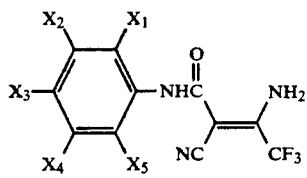

wherein $X_1$, $X_2$, $X_3$, $X_4$, and $X_5$, which may be the same or different, each represents a hydrogen atom, a halogen atom, a substituted or unsubstituted lower alkyl group, a substituted or unsubstituted lower alkoxy group, a lower haloalkyl group, a lower haloalkoxy group, a nitro group, a substituted or unsubstituted lower alkanesulfonyl group, a substituted or unsubstituted alkanesulfonyloxy group, a substituted or unsubstituted benzenesulfonyl group, a substituted or unsubstituted benzenesulfonyloxy group, a substituted or unsubstituted phenoxy group, a substituted or unsubstituted benzyloxy group, a dialkylamino group, a mono- or di-lower alkanesulfonylamino group, a substituted or unsubstituted lower alkylthio group, a $-SO_2R_1$ wherein $R_1$ represents a lower alkyl group or a lower haloalkyl group, a lower alkoxycarbonyloxy group, a substituted or unsubstituted alkoxycarbonyl group, a $-CH=N-OR_2$ group wherein $R_2$ represents a lower alkyl group, a substituted or unsubstituted pyrazolyl-1-yl group, a substituted or unsubstituted pyridyloxy group, or a pyrimidyl group; $X_2$ may be bonded to $X_1$ or $X_3$ to form a ring.

DETAILED DESCRIPTION OF THE INVENTION

In formula (I), $X_1$, $X_2$, $X_3$ and $X_5$, which may be the same or different, each preferably includes a hydrogen atom; a halogen atom; a lower alkyl group which may be substituted with a halogen atom; a lower alkoxy group which may be substituted with a halogen atom; a nitro group; a lower alkanesulfonyl group which may be substituted with a halogen atom; a lower alkanesulfonyloxy group which may be substituted with halogen atoms; a benzenesulfonyl group which may be substituted with a lower alkyl group and/or a halogen atom; a benzenesulfonyloxy group which may be substituted with a lower alkyl group and/or a halogen atom; a phenoxy group which may be substituted with at least one group selected from a halogen atom, a lower haloalkyl group or a lower alkyl group; a benzyloxy group which may be substituted with at least one group selected from a halogen atom, a lower alkyl group, or a lower haloalkyl group; N,N-dialkylamino; N,N-bis-lower alkanesulfonylamino; a lower alkylthio group which may be substituted with a halogen atom; a $-SO_2R_1$ group wherein $R_1$ represents a lower alkyl group or a lower haloalkyl group; a lower alkoxycarbonyloxy group; an alkoxycarbonyl group which may be substituted with a halogen atom; a $-CH=N-OR_2$ group wherein $R_2$ represents a lower alkyl group, a pyrazolyl-1-yl group which may be substituted with a halogen atom and/or a trifluoromethyl group; a pyridyloxy group which may be substituted with a halogen atom nd/or a trifluoromethyl group; or a pyrimidyl group; $X_2$ may be bonded to $X_1$ or $X_3$ to form $-O-CH_2-O-$ or $-O-CF_2-O-$.

The preferred examples of the lower alkyl group and lower alkoxy group used herein include an alkyl group having 1 to 6 carbon atoms, more preferably 1 to 4 carbon atoms and an alkoxy group having 1 to 6 carbon atoms, more preferably 1 to 4 carbon atoms, respectively. The halogen atom preferably includes fluorine, chlorine and bromine.

Specific examples of the crotonic acid amide derivatives represented by formula (I) are shown in Table 1 below. In the Table, s, d, t, q, m, and Br (or br) in NMR values indicate a singlet, a doublet, a triplet, a quartet, a multiplet, and a broad width; CDCl$_3$ and DMSO-d$_6$, solvents for NMR measurements, are deuterium chloroform and deuterium dimethyl sulfoxide, respectively; and the internal standard of the NMR values is tetramethylsilane.

TABLE 1

[Structure: phenyl ring with X1, X2, X3, X4, X5 substituents, attached to NHC(=O)-C(CN)=C(NH2)-CF3]

| Compound No. | X1 | X2 | X3 | X4 | X5 | Melting Point (°C) | NMR δ (60 MHz) |
|---|---|---|---|---|---|---|---|
| 1 | H | H | H | H | H | 162-163 | CDCl3 7.0~7.55(5H, m, ArH), 7.65(1H, Br, s, NHCO), 9.50~10.50(1H, Br, s, NH) |
| 2 | Cl | H | H | H | H | 179-180.5 | CDCl3 + DMSO - d6 6.95~7.40 (4H, m, ArH) |
| 3 | F | H | H | H | H | 146-148 | CDCl3 + DMSO - d6 6.00~7.00(1H, Br, s, NH), 6.90~7.30(4H, m, ArH), 7.95(1H, Br, s, NHCO) |
| 4 | H | OCHF2 | H | H | H | 115 | CDCl3 + DMSO - d6 6.50(1H, t, J$_{H-F}$=72Hz, OCHF2), 6.60~7.70 (4H, m, ArH), 8.40(1H, Br, s, NHCO), 9.00~10.00 (1H, Br, s, NH) |
| 5 | H | CF3 | H | H | H | 136-138 | CDCl3 5.50~7.00(1H, Br, s, NH), 7.10~7.70(4H, m, ArH), 7.80(1H, Br, s, NHCO) |
| 6 | H | OCF3 | H | H | H | 130-132 | CDCl3 + DMSO - d6 6.95(1H, d, J=9Hz, ArH), 7.45(1H, d, J=9Hz, ArH), 8.45(1H, Br, s, NHCO) |
| 7 | H | OCF2CHF2 | H | H | H | 153-156 | CDCl3 + DMSO - d6 2.78(1H, Br, s, NH), 5.00~5.10, 5.90~6.00, 6.80~6.90(1H, m, J$_{H-F}$=54Hz, OCF2CHF2), 6.65~7.55(4H, m, ArH), 8.55(1H, Br, s, NHCO), 9.00~10.00(1H, Br, s, NH) |
| 8 | H | Cl | H | H | H | 164.5-166.5 | CDCl3 5.50~6.70(1H, Br, s, NH), 7.12(4H, m, ArH) 7.55(1H, Br, s, NH), 7.72(1H, Br, s, NHCO) |
| 9 | H | H | CH3 | H | H | 155.5-159 | CDCl3 + DMSO - d6 2.25(3H, s, CH3), 6.90~7.30(4H, m, ArH), 8.00 (1H, Br, s, NHCO) |
| 10 | H | H | OCH3 | H | H | 152-154.5 | CDCl3 + DMSO - d6 3.75(3H, s, OCH3), 6.80(2H, d, J=9Hz, ArH), 7.35(2H, d, J=9Hz, ArH) |
| 11 | H | H | CF3 | H | H | 191-193 | CDCl3 + DMSO - d6 7.35~7.70(4H, m, ArH), 8.65(1H, Br, s, NHCO), 8.50~10.30(2H, Br, s, NH2) |
| 12 | H | H | OCF3 | H | H | 146 | CDCl3 + DMSO - d6 7.00(2H, d, J=9Hz, ArH), 7.42(2H, d, J=9Hz, ArH), 9.20~10.00 (1H, Br, s, NH) |

TABLE 1-continued

![Structure: phenyl ring with X1, X2, X3, X4, X5 substituents, connected via NHC(=O)-C(CN)=C(NH2)(CF3)]

| Compound No. | $X_1$ | $X_2$ | $X_3$ | $X_4$ | $X_5$ | Melting Point (°C.) | NMR δ (60 MHz) |
|---|---|---|---|---|---|---|---|
| 13 | H | H | (3-methyl-4-chloro-phenoxy group: H₃C-, Cl- substituted phenyl-O-) | H | H | 180.5-182 | CDCl₃ 5.30~6.50(1H, Br, s, NH), 2.35(3H, s, —CH₃), 6.00~7.45(7H, m, ArH) |
| 14 | H | H | Cl | H | H | 176.5-177 | CDCl₃ 5.50~6.50(1H, Br, s, NH), 7.27(4H, m, ArH), 7.75(1H, Br, s, NHCO) |
| 15 | H | Cl | H | Cl | H | 192-193.5 | CDCl₃ + DMSO - d₆ 7.32(1H, Br, s, NHCO), 7.44(2H, m, ArH), 8.35 (1H, Br, s, NHCO), 9.50~10.50(1H, Br, s, NH) |
| 16 | H | F | H | F | H | 168-170 | CDCl₃ 6.45~7.25(3H, m, ArH) |
| 17 | H | CH₃ | H | CH₃ | H | 193.5-196 | CDCl₃ + DMSO - d₆ 2.30(6H, s, CH₃), 7.05(2H, s, ArH), 7.015 (1H, s, ArH) |
| 18 | H | C₂H₅ | H | C₂H₅ | H | 160 | CDCl₃ 1.22(6H, t, J=8.0Hz, CH₂CH₃), 2.63(4H, q, J=8.0Hz, CH₂CH₃), 6.78(1H, s, ArH), 7.02 (2H, s, ArH), 7.68(1H, Br, s, NHCO) |
| 19 | H | OCH₃ | H | OCH₃ | H | 188 | CDCl₃ + DMSO - d₆ 3.75(6H, s, OCH₃), 6.15(1H, m, ArH), 6.62 (2H, m, ArH), 7.85(1H, Br, s, NHCO) |
| 20 | H | OCHF₂ | H | OCHF₂ | H | 130-132 | CDCl₃ + DMSO - d₆ 6.45(2H, t, J_{H−F}=72Hz, OCHF₂), 7.20~7.32 (3H, m, ArH), 8.30~10.00(2H, Br, s, NH₂), 8.70 (1H, Br, s, NHCO) |
| 21 | H | CF₃ | H | CF₃ | H | 157.5-159.5 | CDCl₃ 5.70~7.00(1H, Br, s, NH), 7.18(1H, s, ArH), 7.58(1H, Br, s, NH), 8.03(2H, s, ArH), 8.35 (1H, Br, s, NHCO) |
| 22 | H | Cl | Cl | H | H | 165-166 | CDCl₃ + DMSO - d₆ 7.10~8.15(3H, m,ArH), 8.45(1H, Br, s, NHCO), 9.50~10.50(1H, Br, s, NH) |
| 23 | H | Cl | F | H | H | 162-163 | CDCl₃ 5.50~6.50(1H, Br, s, NH), 6.90~7.40(2H, m, ArH, NHCO), 7.50~8.00(2H, m, ArH, NHCO), 9.50~10.20 (1H, Br, s, NH) |
| 24 | H | Cl | OCHF₂ | H | H | 152-154 | CDCl₃ + DMSO - d₆ |

TABLE 1-continued

[Structure: phenyl ring with X1, X2, X3, X4, X5 substituents connected to NHC(=O)-C(CN)=C(NH2)-CF3]

| Compound No. | X1 | X2 | X3 | X4 | X5 | Melting Point (°C.) | NMR δ (60 MHz) |
|---|---|---|---|---|---|---|---|
| 25 | H | CF3 | Cl | H | H | 183-184 | 6.41(1H, t, J_H-F=72Hz, OCHF2), 7.12-7.75 (3H, m, ArH), 8.26(1H, Br, s, NHCO), 9.50~10.50 (1H, Br, s, NH) |
| 26 | H | CF3 | Br | H | H | 192-195 | CDCl3 + DMSO - d6 7.20~8.20(3H, m, ArH), 8.50~9.50(1H, Br, s, NH), 9.10(1H, Br, s, NHCO), 10.00~10.70 (1H, Br, s, NH) |
| 27 | H | NO2 | Cl | H | H | 234-236 | CDCl3 + DMSO - d6 3.00(1H, Br, s, NH), 7.55(2H, m, ArH), 8.00 (1H, d, J=3Hz, ArH), 9.35(1H, Br, s, NHCO) |
| 28 | H | CF3 | CF3 | H | H | 152-153 | CDCl3 + DMSO - d6 7.37(1H, d, J=9Hz, ArH), 7.67~7.88(1H, m, ArH), 8.33(1H, d, J=3Hz, ArH), 8.50~10.50 (2H, Br, s, NH2), 9.35(1H, Br, s, NHCO) |
| 29 | H | CF3 | F | H | H | 141-142 | CDCl3 + DMSO - d6 7.60~8.30(3H, m, ArH), 8.50~10.20(2H, Br, s, NH2), 9.58(1H, Br, s, NHCO) |
| 30 | H | Br | Br | H | H | 173 | CDCl3 + DMSO - d6 6.90~8.00(3H, m, ArH), 9.00(1H, Br, s, NHCO), 9.30~10.50(1H, Br, s, NH) |
| 31 | H | Cl | [isoxazole ring with Cl and CF3 substituents] | H | H | 174-177 | CDCl3 + DMSO - d6 7.25~7.90(3H, m, ArH), 9.50~10.50(1H, Br, s, NH) |
| 32 | Cl | Cl | H | H | H | 215-216 | CDCl3 + DMSO - d6 6.58(1H, s, ArH), 7.15~7.95(3H, m, ArH), 8.50~9.30(1H, Br, s, NHCO), 9.05(1H, Br, s, NH) |
| 33 | Cl | H | Cl | H | H | 198-200 | CDCl3 + DMSO - d6 7.10~8.20(3H, m, ArH), 8.45(1H, Br, s, NHCO), 9.40~10.30(1H, Br, s, NH) |
| 34 | Cl | H | H | Cl | H | 219-220 | CDCl3 + DMSO - d6 7.00~7.50(2H, m, ArH), 8.10(1H, d, J=9Hz, ArH), 8.40(1H, Br, s, NHCO), 8.80~10.00(2H, Br, s, NH2) |
| 35 | Cl | H | H | H | Cl | 136-146 | CDCl3 7.15~7.40(3H, m, ArH), 9.50~10.50(1H, Br, s, |

TABLE 1-continued

[Structure: phenyl ring with substituents X1, X2, X3, X4, X5 and NHC(=O)-C(CN)=C(NH2)(CF3) group]

| Compound No. | X1 | X2 | X3 | X4 | X5 | Melting Point (°C.) | NMR δ (60 MHz) |
|---|---|---|---|---|---|---|---|
| 36 | F | H | H | H | F | 192-196 | CDCl3 + DMSO - d6 6.65~7.30(3H, m, ArH), 8.00(1H, Br, s, NHCO), 9.50~10.00(1H, Br, s, NH) |
| 37 | H | Cl | Cl | Cl | H | 219-222 | CDCl3 + DMSO - d6 3.00(1H, Br, s, NHCO), 7.75(2H, s, ArH), 9.20 (1H, Br, s, NHCO), 9.50~10.50(1H, Br, s, NH) |
| 38 | H | Cl | OCH3 | Cl | H | 207-209 | CDCl3 + DMSO - d6 3.85(3H, s, OCH3), 5.80~6.50(1H, Br, s, NH), 7.40(2H, s, ArH), 7.80(1H, Br, s, NHCO), 9.50~10.20(1H, Br, s, NH) |
| 39 | H | Cl | OC2H5 | Cl | H | 184.5-186.5 | CDCl3 + DMSO - d6 1.42(3H, t, J=7Hz, OCH2CH3), 4.05(2H, q, J=7Hz, OCH2CH3), 7.50(2H, s, ArH), 8.35 (1H, Br, s, NHCO), 7.80~9.00(1H, Br, s, NH) |
| 40 | H | Cl | F | Cl | H | 187-188 | CDCl3 + DMSO - d6 2.80(1H, Br, s, NH), 7.60(2H, d, JH-F=6Hz, ArH), 8.88(1H, Br, s, NHCO), 9.50~10.50 (1H, Br, s, NH) |
| 41 | H | Cl | H3CSO2—O— | Cl | H | 122-125 | CDCl3 + DMSO - d6 3.33(3H, s, CH3), 4.39(2H, Br, s, NH2) 6.58 (2H, s, ArH) |
| 42 | H | Cl | (H3CSO2)2N— | Cl | H | 222-225 | CDCl3 + DMSO - d6 3.55(6H, s, CH3), 7.83(2H, s, ArH), 9.30 (1H, Br, s, NHCO), 9.00~10.00(1H, Br, s, NH) |
| 43 | H | Cl | C6H5CH2—O— | Cl | H | 228-229 | CDCl3 + DMSO - d6 4.95(2H, s, CH2), 7.20~7.60(5H, m, ArH), 7.60 (2H, s, ArH), 8.80(1H, Br, s, NHCO) |
| 44 | H | Cl | 4-H3C-C6H4-SO2—O— | Cl | H | 230.5-233 | CDCl3 + DMSO - d6 2.84(3H, s, CH3), 7.29(2H, s, ArH), 7.60 (4H, s, ArH), 9.00(1H, Br, s, NHCO) |

TABLE 1-continued

| Compound No. | X₁ | X₂ | X₃ | X₄ | X₅ | Melting Point (°C.) | NMR δ (60 MHz) |
|---|---|---|---|---|---|---|---|
| 45 | H | Cl | (isoxazole with Cl, Cl, N-N, CF₃) | Cl | H | 184 | CDCl₃ + DMSO - d₆ 7.86(2H, s, ArH), 9.35(1H, Br, s, NHCO), 9.50~10.50(1H, Br, s, NH) |
| 46 | H | Cl | OCF₂CHFCF₃ | Cl | H | 179 | CDCl₃ + DMSO - d₆ 4.75~5.25, 5.45~5.95(1H, m, $J_{H-F}$=42Hz, OCF₂CHFCF₃), 7.70(2H, s, ArH), 9.15(1H, Br, s, NHCO), 8.50~9.50(1H, Br, s, NH), 9.50~10.00(1H, Br, s, NH) |
| 47 | H | Cl | OCHF₂ | Cl | H | 182-185 | CDCl₃ + DMSO - d₆ 6.49(1H, t, $J_{H-F}$=73Hz, OCHF₂), 7.70(2H, s, ArH), 8.50~9.20(1H, Br, s, NH), 9.00(1H, Br, s, NHCO), 9.50~10.00(1H, Br, s, NH) |
| 48 | H | Cl | (pyridine with Cl, O—, F₃C, N) | Cl | H | 207-209.5 | CDCl₃ 6.00~6.70(1H, Br, s, NH), 7.62(2H, s, ArH), 7.95(2H, s, ArH), 8.15(1H, Br, s, NHCO), 9.50~10.00(1H, Br, s, NH) |
| 49 | Cl | H | Cl | Cl | H | 220-223 | CDCl₃ + DMSO - d₆ 7.45(1H, s, ArH), 8.35(1H, s, ArH), 8.40 (1H, Br, s, NHCO), 9.00~10.00(1H, Br, s, NH) |
| 50 | Cl | H | Cl | H | Cl | 172.5-175.5 | CDCl₃ + DMSO - d₆ 5.50~6.50(1H, Br, s, NH), 7.30(2H, s, ArH), 7.45(1H, Br, s, NHCO), 9.50~10.50(1H, Br, s, NH) |
| 51 | F | F | F | H | H | 175-176.5 | CDCl₃ + DMSO - d₆ 6.60~7.75(2H, m, ArH), 8.13(1H, Br, s, NHCO) |
| 52 | H | Cl | Cl | H | F | 193-195.5 | CDCl₃ + DMSO - d₆ 2.65(1H, Br, s, NH), 7.15(1H, d, $J_{H-F}$=9Hz, ArH), 8.18(1H, d, $J_{H-F}$=6Hz, ArH) |

TABLE 1-continued

[Structure: phenyl ring with substituents X1, X2, X3, X4, X5 bearing -NHC(=O)-C(CN)=C(NH2)-CF3 group]

| Compound No. | X1 | X2 | X3 | X4 | X5 | Melting Point (°C.) | NMR δ (60 MHz) |
|---|---|---|---|---|---|---|---|
| 53 | H | H3CSO2— | Cl | H | F | 168-169 | CDCl3 + DMSO-d6 3.24(3H, s, CH3), 7.10~8.29(2H, m, ArH) |
| 54 | Cl | CF3 | H | Cl | H | 123-133 | CDCl3 + DMSO-d6 2.79(1H, Br, s, NH), 7.37(1H, d, J=3Hz, ArH), 8.48(1H, d, J=3Hz, ArH), 8.63(1H, Br, s, NHCO), 9.00~10.00(1H, Br, s, NH) |
| 55 | F | CF3 | H | Cl | H | 153-158 | CDCl3 + DMSO-d6 7.24(1H, m, $J_{H-F}$=9Hz, ArH), 8.31(1H, m, $J_{H-F}$=9Hz, ArH) |
| 56 | Cl | H | Cl | CF3 | H | 157-159 | CDCl3 + DMSO-d6 7.50(1H, s, ArH), 8.45(1H, Br, s, NHCO), 8.64 (1H, s, ArH) |
| 57 | F | Cl | F | Cl | H | 143-152 | CDCl3 + DMSO-d6 8.05(1H, dd, $J_{H-F}$=9Hz, ArH) |
| 58 | F | F | F | F | F | 160-164 | CDCl3 + DMSO-d6 8.85(2H, Br, s, NH, NHCO), 9.80(1H, Br, s, NH) |
| 59 | F | F | Br | F | F | 183.5-185 | CDCl3 + DMSO-d6 8.25(2H, Br, s, NH, NHCO), 9.80(1H, Br, s, NH) |
| 60 | F | Cl | [3-CF3-phenoxy group] | Cl | H | 149-160 | CDCl3 + DMSO-d6 6.80~8.50(5H, m, ArH), 8.50~10.00(1H, Br, s, NH), 10.00~11.00(1H, Br, s, NH) |
| 61 | F | Cl | (H5C2)2N— | Cl | H | 218-219.5 | CDCl3 + DMSO-d6 1.05(6H, t, J=9Hz, CH2CH3), 3.15(4H, q, J=9Hz, CH2CH3), 8.35(1H, d, $J_{H-F}$=9Hz), 8.20~9.00(1H, Br, s, NH), 9.85(1H, Br, s, NHCO) |
| 62 | H | F | Cl | H | OCHF2 | 113-114 | CDCl3 + DMSO-d6 11.00~8.50(2H, Br, s, NH2), 8.33(1H, Br, s, NHCO), 8.13(1H, d, $J_{H-F}$=12Hz, ArH), 7.14 (1H, d, $J_{H-F}$=9Hz, ArH), 6.60(1H, t, $J_{H-F}$=72Hz, OCHF2) |
| 63 | Cl | Cl | H | CF3 | H | 156-157 | CDCl3 + DMSO-d6 |

TABLE 1-continued

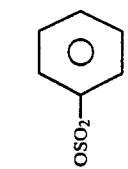

| Compound No. | $X_1$ | $X_2$ | $X_3$ | $X_4$ | $X_5$ | Melting Point (°C.) | NMR δ (60 MHz) |
|---|---|---|---|---|---|---|---|
| 64 | H | Cl | Cl | H | $CF_3$ | 172-173 | 10.50~8.50(2H, Br, s, $NH_2$), 8.60(1H, Br, s, NHCO), 8.50(1H, d, J=2Hz, ArH), 7.42(1H, d, J=2Hz, ArH) |
| 65 | H | Cl | F | H | $CF_3$ | 135-138 | $CDCl_3$ + DMSO - $d_6$ 11.00~8.50(2H, Br, s, $NH_2$), 8.30(1H, Br, s, NHCO), 8.22(1H, s, ArH), 7.60(1H, s, ArH) |
| 66 | H | $OCHF_2$ | Cl | H | F | 165-167 | $CDCl_3$ + DMSO - $d_6$ 11.00~9.00(2H, Br, s, $NH_2$), 8.20(1H, Br, s, NHCO), 8.10(1H, d, $J_{H-F}$=9Hz, ArH) 7.35 (1H, d, $J_{H-F}$=12Hz, ArH) |
| 67 | H | [cyclohexyl]$OSO_2$ | Cl | H | F | 191-199 | $CDCl_3$ + DMSO - $d_6$ 10.00~8.00(2H, Br, s, $NH_2$), 8.10(1H, d, $J_{H-F}$=9Hz, ArH), 8.10(1H, Br, s, NHCO), 7.12 (1H, d, $J_{H-F}$=12Hz, ArH), 6.42(1H, t, $J_{H-F}$=72Hz, $OCHF_2$) |
| 68 | H | $OCF_2CFHCF_3$ | Cl | H | F | 141-142 | $CDCl_3$ + DMSO - $d_6$ 11.00~8.50(2H, Br, s, $NH_2$), 8.21(1H, Br, s, NHCO), 8.05(1H, d, $J_{H-F}$=9Hz, ArH), 7.85~7.35 (5H, m, ArH), 7.08(1H, d, $J_{H-F}$=12Hz, ArH) |
| 69 | H | $OCF_2CFHCF_3$ | F | H | F | 108-110 | $CDCl_3$ 11.00~9.00(2H, Br, s, $NH_2$), 8.20(1H, d, $J_{H-F}$=9Hz, ArH), 7.95(1H, Br, s, NHCO), 7.18 (1H, d, $J_{H-F}$=12Hz, ArH), 5.50~4.40(1H, m, $J_{H-F}$=42Hz, $OCF_2CHFCF_3$) |
| 70 | H | Cl | $OCF_2CFHCF_3$ | H | Cl | 186-187 | $CDCl_3$ 11.00~9.00(2H, Br, s, $NH_2$), 8.05(1H, t, $J_{H-F}$=9Hz, ArH), 7.80(1H, Br, s, NHCO), 6.90 (1H, t, $J_{H-F}$=12Hz, ArH), 5.50~4.40(1H, m, $J_{H-F}$=42Hz, $OCF_2CHFCF_3$) |
| 71 | H | $OCH(CH_3)_2$ | Cl | H | Cl | 113-115 | $CDCl_3$ + DMSO - $d_6$ 11.00~9.00(2H, Br, s, $NH_2$), 8.36(1H, s, ArH), 8.35(1H, Br, s, NHCO), 7.30(1H, s, ArH), 5.70~4.50(1H, m, $J_{H-F}$=42Hz, $OCF_2CHFCF_3$) |
| 72 | H | $OCH(CH_3)_2$ | F | H | F | 242-247 | $CDCl_3$ 11.00~9.00(2H, Br, s, $NH_2$), 8.30(1H, Br, s, NHCO), 7.90(1H, s, ArH), 7.25(1H, s, ArH), 4.70~4.20(1H, m, $OCH(CH_3)_2$), 1.35(6H, d, J=6Hz, $OCH(CH_3)_2$) |

TABLE 1-continued

| Compound No. | $X_1$ | $X_2$ | $X_3$ | $X_4$ | $X_5$ | Melting Point (°C.) | NMR δ (60 MHz) |
|---|---|---|---|---|---|---|---|
| 73 | H | Cl | OCHF$_2$ | H | Cl | 200–203 | 11.00~9.00(2H, Br, s, NH$_2$), 7.85(1H, Br, s, NHCO), 7.65(1H, t, $J_{H-F}$=9Hz, ArH), 6.80 (1H, t, $J_{H-F}$=12Hz, ArH), 4.70~4.10(1H, m, OCH(CH$_3$)$_2$), 1.35(1H, d, $J_{H-F}$=6Hz, OCH(CH$_3$)$_2$) |
| 74 | H | (pyridinone-CF$_3$/Cl) | H | H | H | 185–187 | CDCl$_3$ + DMSO - d$_6$ 11.00~9.00(2H, Br, s, NH$_2$), 8.30(1H, Br, s, NHCO), 7.90(1H, s, ArH), 7.25(1H, s, ArH), 4.70~4.20(1H, m, OCH(CH$_3$)$_2$), 1.35(6H, d, J=6Hz, OCH(CH$_3$)$_2$) |
| 75 | H | (pyridinone-CF$_3$/Cl) | Cl | H | H | 185–187 | CDCl$_3$ + DMSO - d$_6$ 10.00~8.00(2H, Br, s, NH$_2$)8.32(1H, Br, s, NHCO), 8.32~6.55(6H, m, ArH) |
| 76 | H | phenyl | H | H | H | 183–185 | CDCl$_3$ + DMSO - d$_6$ 11.00~9.00(2H, Br, s, NH$_2$), 8.39(1H, Br, s, NHCO), 8.19(1H, s, ArH), 8.10~7.75(2H, m, ArH), 7.40(1H, s, ArH) |
| 77 | H | H | SCF$_2$H | H | H | 138–139 | CDCl$_3$ + DMSO - d$_6$ 10.5~9.20(m)3H NH NH$_2$ 7.5~6.20(m)9H aromatic |
| 78 | H | (pyridinone) | H | H | H | 145–147 | CDCl$_3$ + DMSO - d$_6$ 10.00~8.50(2H, Br, s, NH$_2$), 8.32(1H, Br, s, NHCO), 7.45(4H, s, ArH), 6.70(1H, t, $J_{H-F}$=72Hz, SCHF$_2$) |
|  |  |  |  |  |  | 189–190 | CDCl$_3$ + DMSO - d$_6$ 10.2~9.0(m)3H NH, NH$_2$ 8.8~6.9(m)8H aromatic |

TABLE 1-continued

[Structure: phenyl ring with X1, X2, X3, X4, X5 substituents, attached via NHC(=O)-C(CN)=C(NH2)-CF3]

| Compound No. | X1 | X2 | X3 | X4 | X5 | Melting Point (°C.) | NMR δ (60 MHz) |
|---|---|---|---|---|---|---|---|
| 79 | H | [4-CF3, 2-Cl pyridin-6(1H)-one-N-yl] | H | CF3 | H | 191–192 | CDCl3 + DMSO - d6 9.9~9.0(m)3H NH, NH2 8.8~7.3(m)5H aromatic |
| 80 | H | [pyridin-2(1H)-one-N-yl] | H | CF3 | H | 138–140 | CDCl3 9.8~8.9(m)3H NH, NH2 8.4~6.9(m)7H aromatic |
| 81 | H | OCH2C≡CH | H | CF3 | H | 98–99 | CDCl3 10.2~9.0(m)3H NH, NH2 8.0~7.1(m)3H aromatic 4.6(d)J=3Hz(2H —CH2—O—) 2.6~2.5(m)1H CH≡C |
| 82 | F | H | OCOC2H5 | CH3 | H | 192–194 | CDCl3 + DMSO - d6 10.00~8.50(2H, Br, s, NH2), 8.00(1H, Br, s, NHCO), 8.00~6.70(2H, m, ArH), 3.95(2H, q, J=9Hz, OCH2CH3), 2.18(3H, s, CH3), 1.40(3H, t, J=9Hz, OCH2CH3) |
| 83 | H | [oxazol-2(3H)-one-N-yl] | H | CF3 | H | 161–162 | CDCl3 + DMSO - d6 10.0~8.8(m)3H NH, NH2 8.7~7.0(m)6H aromatic |
| 84 | H | OCF2Br | H | CF3 | H | 63–65 | CDCl3 10.2~9.1(m)3H NH, NH2 8.1~7.3(m)3H aromatic |
| 85 | H | OCF2H | H | CF3 | H | 123–124 | CDCl3 9.9~9.0(m)3H NH, NH2 8.3~7.3(m)3H aromatic 6.6(t)J=68Hz 1H —CHF2 |
| 86 | Cl | CF3 | H | Br | H | 152–153 | CDCl3 + DMSO - d6 |

TABLE 1-continued

![structure: phenyl ring with X1, X2, X3, X4, X5 substituents and NHC(=O)–C(NC)=C(NH2)(CF3) group]

| Compound No. | X₁ | X₂ | X₃ | X₄ | X₅ | Melting Point (°C.) | NMR δ (60 MHz) |
|---|---|---|---|---|---|---|---|
| 87 | H | CF₃ | H | Br | Cl | 172–174 | 9.9~8.8(m)3H NH, NH₂<br>8.3(s)1H aromatic<br>7.6(s)1H aromatic<br>CDCl₃ + DMSO-d₆ |
| 88 | H | H | Cl | CH=NOCH₃ | H | 161–162 | 9.9~9.0(m)3H NH NH₂<br>8.1(s)1H aromatic<br>7.8(s)1H aromatic<br>CDCl₃ + DMSO-d₆<br>9.6~9.0(m)3H NH NH₂<br>3.9(s)3H —OCH₃<br>8.2(s)1H —CH=<br>8.0(d)1H J=2Hz aromatic<br>7.6~7.1(m) 2H aromatic |
| 89 | H | Cl | SCF₂H | H | H | 159–160 | CDCl₃ + DMSO-d₆<br>9.8~9.2(m) 3H NH, NH₂<br>8.0(s)1H aromatic<br>7.5(s)2H aromatic |
| 90 | CF₃ | H | H | H | H | 153–157 | 7.2(t)1H J=36Hz CHF₂<br>CDCl₃ + DMSO 1 d₆<br>7.0~8.5(4H, m, ArH) |
| 91 | H | Cl | SCF₂CF₂H | H | H | 147–148 | CDCl₃ + DMSO-d₆<br>9.8~9.0(m)3H NH, NH₂<br>7.9(s)1H aromatic<br>7.5(s)1H aromatic |
| 92 | H | Cl | SCF₂CFClH | H | H | 118–120 | 6.8~5.0(m)1H J_{H–F}=46Hz 1H<br>CDCl₃ + DMSO-d₆<br>9.9~9.0(m)3H NH, NH₂<br>7.9, 7.5(s)1H, 2H aromatic |
| 93 | H | F | SCF₂CF₂H | H | H | 144–146 | 7.0~6.0(m)1H J_{H–F}=42Hz<br>DMSO + CDCl₃-d₆<br>9.7~9.0(m)3H NH, NH₂<br>7.8~7.3(m)3H aromatic |
| 94 | H | H | Cl | H | CF₃ | 190 | 7.0~5.2(m)1H J_{H–F}=46Hz<br>CDCl₃ + DMSO-d₆<br>7.2~8.2(3H, m, ArH) |
| 95 | Cl | H | H | CF₃ | H | 206–210 | CDCl₃ + DMSO-d₆<br>9.2~10.5(3H, br, NHCO, NH₂), 8.3~8.7(3H, ArH) |
| 96 | H | CN | Cl | H | H | <250 | CDCl₃ + DMSO-d₆<br>9.2~9.7(3H, br, NHCO, NH₂) 7.2~8.1<br>(3H, br, ArH) |
| 97 | F | H | SCF₂CF₂H | H | H | 138–140 | CDCl₃ + DMSO-d₆<br>9.9~8.2(m)3H NH, NH₂ |

TABLE 1-continued

Structure: Phenyl ring with substituents $X_1, X_2, X_3, X_4, X_5$ attached to a group —NHC(=O)—C(CN)=C(NH_2)—CF_3

| Compound No. | $X_1$ | $X_2$ | $X_3$ | $X_4$ | $X_5$ | Melting Point (°C.) | NMR δ (60 MHz) |
|---|---|---|---|---|---|---|---|
| 98 | F | H | SCF_2CF_2H | F | H | 128-129 | 8.1~7.9(m)1H aromatic 7.6~7.2(m)2H aromatic 7.1~5.1(m)1H $J_{H-F}$=47Hz CDCl_3 + DMSO - d_6 10.0~9.0(m)2H NH_2 8.8~8.3(m)1H NH |
| 99 | F | Cl | SCF_2CFClH | H | H | — | 8.2~7.9(m)1H aromatic 7.5~7.3(m)1H aromatic 7.1~5.2(m)1H $J_{H-F}$=46Hz |
| 100 | F | H | SCF_2CFClH | Cl | H | — | |
| 101 | H | CH_3 | H | OCF_2CF_2H | H | 129-131 | 9.9~8.2(m)3H NH, NH_2 7.9~7.3(m)3H aromatic 7.3~5.6(m)1H $J_{H-F}$=45Hz CDCl_3 + DMSO - d_6 10.0~9.0(m)2H NH_2 |
| 102 | F | H | SCF_2CF_2H | Br | H | 173-174 | 9.1~8.7(m)1H NH 8.4(d)$J$=8Hz 1H aromatic 7.55(d)$J$=12Hz 1H aromatic 7.0~5.3(m)$J_{H-F}$=46Hz 1H |
| 103 | H | CF_3 | H | SCF_2CF_2H | H | — | |
| 104 | H | CF_3 | H | SCF_2CFClH | H | — | |
| 105 | F | SCHF_2 | Cl | Cl | H | — | |
| 106 | F | H | H | Br | H | — | |
| 107 | F | CF_3 | H | CF_3 | H | — | |
| 108 | F | Br | H | CF_3 | H | — | |
| 109 | F | Cl | H | | H | — | |
| 110 | H | —OCF_2O— (X_2–X_3 bridge) | | H | H | 158-159 | CDCl_3 + DMSO - d_6 11.00~9.00(2H, Br, s, NH_2), 8.21(1H, Br, s, NHCO), 7.40(1H, s, ArH), 6.90(2H, s, ArH) |
| 111 | H | —OCH_2O— (X_2–X_3 bridge) | | H | H | 166-167 | CDCl_3 + DMSO - d_6 11.00~9.00(2H, Br, s, NH_2), 7.95(1H, Br, s, NHCO), 7.05(1H, s, ArH), 5.85(2H, s, ArH) |
| 112 | H | Cl | CN | Cl | H | — | |
| 113 | H | CO_2CH_3 | Cl | H | H | 173-174 | CDCl_3 + DMSO - d_6 11.00~9.00(2H, Br, s, NH_2), 8.55(1H, Br, s, NHCO), 7.95(1H, s, J=2Hz, ArH), 7.60 |

TABLE 1-continued

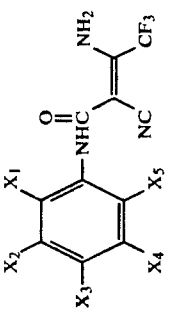

| Compound No. | $X_1$ | $X_2$ | $X_3$ | $X_4$ | $X_5$ | Melting Point (°C.) | NMR δ (60 MHz) |
|---|---|---|---|---|---|---|---|
| 114 | H | $CO_2C_2H_5$ | Cl | H | H | 163-169 | (1H, dd, J=9Hz&2Hz, ArH), 7.25(1H, s, J=9Hz, ArH), 3.85(3H, s, CH$_3$) CDCl$_3$ + DMSO - d$_6$ 11.00~9.00(2H, Br, s, NH$_2$), 8.68(1H, Br, s, NHCO), 7.90(1H, s, J=2Hz, ArH), 7.58(1H, dd, J=9Hz&2Hz, ArH), 7.20(1H, s, J=9Hz, ArH), 4.30(2H, q, J=7Hz, C$\underline{H_2}$CH$_3$), 1.40(3H, t, J=7Hz, CH$_2$C$\underline{H_3}$) |
| 115 | H | $CO_2C_3H_7(n)$ | Cl | H | H | — | — |
| 116 | H | $CO_2C_3H_7(i)$ | Cl | H | H | — | — |
| 117 | H | $CO_2CH_2CF_3$ | Cl | H | H | — | — |
| 118 | H | Cl | $CO_2CH_3$ | H | H | — | — |
| 119 | H | Cl | $CO_2C_2H_5$ | H | H | — | — |
| 120 | H | Cl | $CO_2C_3H_7(n)$ | H | H | — | — |
| 121 | H | Cl | $CO_2C_3H_7(i)$ | H | H | — | — |
| 122 | H | Cl | $CO_2CH_2CF_3$ | H | H | — | — |
| 123 | F | H | Cl | H | H | — | — |
| 124 | F | H | Cl | $OCH_3$ | H | — | — |
| 125 | F | H | Cl | $OC_2H_5$ | H | — | — |
| 126 | F | H | Cl | $OCH_2C\equiv CH$ | H | — | — |
| 127 | F | H | Cl | $SCH_3$ | H | — | — |
| 128 | F | H | Cl | $SC_2H_5$ | H | — | — |
| 129 | F | H | Cl | $SC_3H_7(n)$ | H | — | — |
| 130 | F | H | Cl | $SC_3H_7(i)$ | H | — | — |
| 131 | F | H | Cl | $SCF_2CF_2H$ | H | — | — |
| 132 | F | H | F | $SCF_2H$ | H | — | — |
| 133 | F | H | F | $SCF_2CF_2H$ | H | — | — |
| 134 | H | $SO_2N(CH_3)_2$ | $SO_2CHF_2$ | H | H | — | — |
| 135 | H | Cl | $SCH_3$ | H | H | — | — |
| 136 | H | Cl | $SC_2H_5$ | H | H | — | — |
| 137 | H | $SCF_2CF_2H$ | Cl | H | H | — | — |

The crotonic acid amide derivative represented by formula (I) can be prepared by reacting a cyanoacetanilide represented by formula (II):

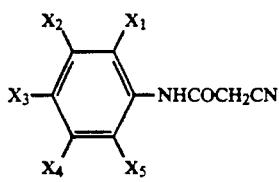

wherein $X_1$, $X_2$, $X_3$, $X_4$, and $X_5$ are as defined above, with trifluoroacetonitrile usually of from 1 to 5 equivalents in a solvent in the presence of from 0.1 to 2 equivalents of a base at a temperature of from $-80°$ C. to the boiling point of the solvent for a period of from 0.5 to 24 hours.

Suitable solvents which can be used include aromatic hydrocarbons, e.g., benzene, toluene, and xylene; ethers, e.g., diethyl ether diisopropyl ether, dioxane, tetrahydrofuran, and dimethoxyethane; and alcohols, e.g., methyl alcohol and ethyl alcohol. Suitable bases which can be used include alkali hydroxides, e.g., sodium hydroxide and potassium hydroxide; carbonates, e.g., sodium carbonate, potassium carbonate, and sodium hydrogencarbonate; acetates, e.g., sodium acetate and potassium acetate; and alkali hydrides, e.g., sodium hydride and potassium hydride; with sodium acetate and potassium acetate being preferred.

After completion of the reaction, the desired compound can be isolated by ordinary work-up procedures. For example, the reaction mixture is concentrated, the concentrate is extracted with an organic solvent, and the extract is washed with water and dried or concentrated. If desired, the product may be purified by silica gel chromatography or recrystallization.

The cyanoacetanilide represented by formula (II) can be prepared by the condensation reaction with cyanoacetyl chloride and the corresponding aniline, the reaction cyanogenating the corresponding chloroacetanilide with potassium cyanide, or the reaction dehydrating the corresponding aniline and cyanoacetic acid with a dehydrating reagent such as dicyclohexylcarbodiimide (hereinafter abbreviated as DCC).

Synthesis Examples of the crotonic acid amide derivatives according to the present invention are shown below.

SYNTHESIS EXAMPLE 1

Synthesis of N-[3,5-bis(trifluoromethyl)]-2-cyanoacetanilide (a) In 300 ml of methylene chloride were dissolved 10.0 g (43.7 mmol) of 3,5-bis(trifluoromethyl)aniline and 5.3 g (52.4 mmol) of triethylamine, and 5.9 g (52.4 mmol) of chloroacetyl chloride was added dropwise to the solution over 10 minutes under ice-cooling. After stirring at room temperature for 3 hours, the reaction mixture was poured into ice-water and washed with water. The organic layer was dried over anhydrous sodium sulfate, and the methylene chloride was removed by distillation under reduced pressure. The resulting pale brown crude crystals were recrystallized from ethyl acetate to obtain 12.0 g (90%) of N-[3,5-bis(-trifluoromethyl)]-2-chloroacetanilide as a white crystal.

(b) In 50 ml of dimethyl sulfoxide were dissolved 12.0 g (39.3 mmol) of N-[3,5-bis(Trifluoromethyl)]-2-chloroacetanilide, and 2.8 g (43.1 mmol) of potassium cyanide dissolved in 3 ml of water was added dropwise thereto over 10 minutes at room temperature. After stirring at room temperature for 3 hours, the reaction mixture was poured into water and extracted twice with 200 ml portions of ethyl acetate. The organic layer was washed twice with a saturated sodium chloride aqueous solution. The extract was dried over anhydrous sodium sulfate, and the ethyl acetate was removed by distillation under reduced pressure. The residue was subjected to silica gel chromatography to obtain 9.3 g (72%) of N-[3,5-bis(trifluoromethyl)]-2-cyanoacetanilide as a white crystal. The yield based on the starting aniline was 72%.

SYNTHESIS EXAMPLE 2

Synthesis of N-[3,5-bis(trifluoromethyl)-2-cyanoacetanilide

In 10 ml of methylene chloride was dissolved 5.0 g (21.8 mmol) of 3,5-bis(trifluoromethyl)aniline, and 2.2 g (25.9 mmol) of cyanoacetic acid was added to the solution. To the solution was further added dropwise 5.8 g (28.2 mmol) of DCC dissolved in 3 ml of methylene chloride over 10 minutes under ice-cooling. The mixture was stirred under ice-cooling for an additional 1 hour, and the suspending solid was removed by filtration. The filtrate was poured into water and extracted twice with methylene chloride. The organic layer was washed successively with a 3M hydrochloric acid aqueous solution, a saturated sodium hydrogencarbonate aqueous solution and a saturated sodium chloride aqueous solution and dried over anhydrous magnesium sulfate. The methylene chloride solvent was removed by distillation under reduced pressure, and the residue was subjected to silica gel chromatography to obtain 5.4 g (84%) of the entitled compound as a white crystal.

SYNTHESIS EXAMPLE 3

Synthesis of 3-amino-N-[3,5-bis(trifluoromethylphenyl)-2-cyano-4,4,4-trifluorocrotonamide In 200 ml of a 1:1 (by volume) mixed solvent of ethanol and dimethoxyethane was dissolved 5.0 g (16.9 mmol) of N-[3,5-bis(trifluoromethyl)]-2-cyanoacetanilide, and 1.5 g (18.3 mmol) of anhydrous sodium acetate was added to the solution. Into the solution was blown 50.7 mmol of trifluoroacetonitrile gas with stirring over 3 hours while keeping the solution at $-78°$ C. The reaction temperature was gradually elevated up to room temperature over 1 day while stirring. The ethanol-dimethylethane solvent was removed by distillation under reduced pressure, and the residue was dissolved in 200 ml of ethyl acetate, washed successively with water and a saturated sodium chloride aqueous solution, and dried over anhydrous sodium sulfate.

The ethyl acetate was removed by distillation under reduced pressure, and the residue was subjected to silica gel chromatography to obtain the desired product as a white crystal, which was then recrystallized from methylene chloride to obtain 5.5 g (83%) of the entitled compound as a white needle-like crystal.

The structure of the resulting compound, including the cis-relation of the carbonyl group and the amino group in the acid moiety thereof, was analyzed by X-ray diffractometry.

The trifluoroacetonitrile gas used was synthesized in accordance with the process described, e.g., in J.A.C.S., Vol. 65, pp. 1458-1460.

SYNTHESIS EXAMPLE 4

Synthesis of N-(3,4-ditrifluoromethyl)-2-cyanoacetanilide

In 100 ml of ethyl acetate was dissolved 5.0 g (21.8 mmol) of 3,4-ditrifluoromethylaniline, and 3.0 g (30 mmol) of triethylamine was added to the solution. To the solution was added dropwise 3.12 g (30 mmol) of cyanoacetyl chloride dissolved in 10 ml of ethyl acetate over 10 minutes under ice-cooling. The mixture was stirred at room temperature for an additional 2 hours, and the suspending solid was removed by filtration. The filtrate was washed with a 1N-hydrochloric acid aqueous solution and a saturated sodium chloride aqueous solution and dried over anhydrous magnesium sulfate. The ethyl acetate solvent was removed by distillation under reduced pressure, and the residue was recrystallized from dichloromethane. The yield was 5.8 g as a white crystal.

SYNTHESIS EXAMPLE 5

Synthesis of Compound 28

To 50 ml of anhydrous dimethoxyethane were added 0.8 g of sodium hydride (60% dispersion in mineral oil), and 5.0 g of N-(3,4-ditrifluoromethyl)-2-cyanoacetanilide was portionwise added to the solution. The solution was stirred at room temperature for 1 hour. Into the solution was added 5.7 g of trifluoroacetonitrile gas with vigorous stirring over 3 hours at room temperature. The solution was poured onto ice water with stirring, and extracted with ethyl acetate. The organic extracts were washed with saturated sodium chloride aqueous solution and dried over anhydrous magnesium sulfate. The solvent was removed by distillation under reduced pressure and the residue was recrystallized from dichloromethane. The yield was 5.5 g as a white needle crystal.

The insecticide according to the present invention have insecticidal activity on Diptera, Coleoptera, Hemiptera, Orthoptera, Isoptera, and Acarina and particularly on Lepidoptera, e.g., *Spodootera litura, Plutella xylostella*, etc.

Noxious insects on which the crotonic acid amide derivatives of the present invention exert insecticidal activity are shown below for illustrative purposes only but not for limitation.

1. Diptera

Muscidae

*Musca domestica vicina, Muscina stabulans, Fannia canicularis*
Culicidae
*Culex pipiens pallens, Culex pipiens molestus, Culex tritaeniorhyncus, Aedes albopictus, Aedes togoi, Armigeres subalbatus, Anopheles hyrcanus sinensis*

2. Coleoptera

*Callosobruchus chinensis, Epilachna vigintioetomaculata, Leptinotarsa decenlineata, Lissorhoptrus oryzochilus*

3. Lepidoptera

*Pieris rapae, Spodoptera litura, Mamestra brassicae, Chilo suppressalis, Ostriria furuacalis, Agrotis fucosa, Plutella maculipennis, Heliothis virescens, Monduca sexta, Plutella xylostella*

4. Hemiptera

*Nephotettix cincticeps, Laodelchax striatellus, Myzus persicae, Aphis gossypii*

5. Orthoptera

*Blatella germanica, Locusta migratoria*

6. Isoptera

*Coptotermes formosanus*

7. Acarina

*Tetranychus urticae, Panonychus citri*

On application of the insecticide of the present invention, the crotonic acid amide derivative of formula (I) may be used as it is but, for the sake of ease of use, it is generally compounded with carriers to formulate into insecticidal preparations, which are diluted if necessary on use. It can be formulated, without any particular limitations, into arbitrary forms, such as emulsifiable concentrates, wettable powders, dusts, granules, and the like by techniques well-known in the field of pesticides. Carriers which can be used include inorganic substances, e.g., clays, talc, bentonite, calcium carbonate, diatomaceous earth, zeolite, and silicic acid anhydride; organic substances of vegetable-origin, e.g., wheat, starch, and crystalline cellulose; high-molecular weight compounds, e.g., petroleum resin, polyvinyl chloride, and polyalkylene glycols; urea; and waxes. Liquid carriers which can be used include various oils, organic solvents, and water. If desired, various adjuvants necessary for formulation, such as wetting agents, dispersing agents, fixing agents, and spreaders, may also be used either individually or in combinations thereof. Adjuvants to be used for wetting, dispersion, spreading, stabilization of ingredients, and rust inhibition include various surface active agents and high-molecular weight compounds, e.g., gelatin, albumin, sodium alginate, methyl cellulose, carboxymethyl cellulose, polyvinyl alcohol, and xanthane gum. Examples of usable surface active agents include nonionic surface active agents, such as polyethylene oxide adducts of alkylphenols, higher alcohols, alkylnaphthols, higher fatty acids, fatty acid esters, or dialkylphosphoric acid amine, etc. and ethylene oxide-propylene oxide copolymers; anionic surface active agents, such as alkylsulfates (e.g., sodium laurylsulfate), alkylsulfonates (e.g., sodium 2-ethylhexylsulfonate), and arylsulfonates (e.g., sodium lignin sulfonate and sodium dodecylbenzenesulfonate); and various cationic and amphoteric surface active agents.

The insecticide of the present invention can be mixed with other physiologically active substances to prepare multi-purpose pesticides. Examples of such physiologically active substances include bactericides, nematocides, herbicides, plant growth regulators, fertilizers, BT chemicals, nuclear polyhederosis viruses, insect hormones as well as insecticides and acaricides. Specific but non-limiting examples of these physiologically active substances include pyrethroids and prethroid double compounds, e.g., Etofenblocks (2-(4-ethoxyphenyl)-2-methylpropyl 3-phenoxybenzyl ether), Fenvalerate (3-phenoxy-α-cyanobenzyl α-isopropyl-4-chlorophenylacetate), Permethrin (3-phenoxybenzyl 3-(2,2-dichlorovinyl)-2,2-dimethylcyclopropane-1-carboxylic acid ester), Cypermethrin (3-phenoxy-α-cyanobenzyl 3-(2,2-dichlorovinyl)-2,2-dimethylcyclopropane-1-carboxylic acid ester), Deltamethrin (3-phenoxy-α-cyanobenzyl3-(2,2-dibromovinyl)-2,2-dimethylcyclopropane-1-carboxylic acid ester), and an insect flower extract; organophosphorus insecticides, e.g., Pyridafenthion (o,o-diethyl-o-(3-oxo-2N-phenyl-2H-pyridazin-6-yl)phosphorothioate), DDVP (o,o-dimethyl-o-(2,2-dichlorovinyl) phosphate), and Fenitrothion (o,o-dimethyl-o-(3-methyl-4-nitrophenyl)phosphorothioate); carbamate insecticides, e.g., NAC (1-naphthyl-N-methylcarbamate), MTMC (meta-tolyl-N-methylcarbamate), and Pirimicarb (Pirimor) (2-dimethylamino-5,6-dimethylpyrimidin-4-yl dimethylcarbamate); skin formation inhibitory agents, e.g., Buprofezin (2-t-butylimino-3-isopropyl-5-phenyl-3,4,5,6-tetrahydro-2H-1,3,5-thiadiazin-4-one) and CME 134 (1-(3,5-dichloro-2,4-difluorophenyl)-3-(2,6-difluorobenzoyl-)urea); bactericides, e.g., Phthalide (4,5,6,7-tetrachlorophthalide), IBP (S-benzyl diisopropylphosphorothioate), EDDP (o-ethyl diphenylphosphorodithioate), Benomyl (methyl 1-(butylcarbamoyl)-2-benzimidazolecarbamate), Probenazole (3-allyloxy-1,2-benzisothiazole-1,1-dioxide), Isoprothiolane (diisopropyl-1,3-dithiolan-2-ylidene malonate), and Tricyclazole (5-methyl-1,2,4-triazolo(3,4-b)benzothiazole); and acaricides, e.g., Kelthane (2,2,2-trichloro-1,1-bis(p-chlorophen-yl)ethanol), Amitraz (3-methyl-1,5-bis(2,4-xylyl))-1,3,5-triazapenta-1,4-diene), and tricyclohexyltin hydroxide.

The content of the active ingredient in the insecticide according to the present invention ranges from 0.001 to 95% by weight, and preferably from 0.1 to 70% by weight.

Preparation Examples of the insecticide of the present invention are shown below, but it should be understood that the present invention is not deemed to be limited thereto. All the percents and parts are by weight unless otherwise specified.

PREPARATION EXAMPLE 1

Dust

A mixture of 3 parts of the compound of the present invention, 10 parts of Carplex #80 (white carbon produced by Shionogi & Co., Ltd.) and 87 parts of clay was ground to obtain 100 parts of a powder containing 3% of the active ingredient.

PREPARATION EXAMPLE 2

Dust

A mixture of 0.5 part of the compound of the present invention, 49.5 parts of calcium carbonate, and 50 parts of clay was ground to obtain 100 parts of a powder containing 0.5% of the active ingredient.

PREPARATION EXAMPLE 3

Wettable Powder

A mixture of 50 parts of the compound of the present invention, 5 parts of Sorpol (surfactant produced by Toho Chemical Industrial Co., Ltd.), and 45 parts of Radiolite (calcined diatomaceous earth produced by Showa Kagaku K.K.) was uniformly ground to obtain 100 parts of a wettable powder containing 50% of the active ingredient.

PREPARATION EXAMPLE 4

Wettable Powder

A mixture of 10 parts of the compound of the present invention, 10 parts of Carplex #80, 3 parts of Emal 10 (surfactant produced by Kao Co., Ltd.), and 77 parts of clay was uniformly ground to obtain 100 parts of a wettable powder containing 10% of the active ingredient.

PREPARATION EXAMPLE 5

Granules

One part of the compound of the present invention, 2 parts of sodium dodecylbenzenesulfonate, 1 part of sodium lignin sulfonate, 25 parts of talc, and 71 parts of bentonite were uniformly mixed and kneaded with water, and the blend was granulated by means of an extrusion granulator, dried, and size-regulated to obtain 100 parts of granules containing 1% of the active ingredient.

PREPARATION EXAMPLE 6

Granules

Three parts of the compound of the present invention, 3 parts of carboxymethyl cellulose, 2 parts of sodium lignin sulfonate, and 92 parts of clay were uniformly mixed and kneaded with water, and the blend was granulated by means of an extrusion granulator, dried and size-regulated to obtain 100 parts of granules containing 3% of the active ingredient.

PREPARATION EXAMPLE 7

Mixed Wettable Powder

Twenty parts of the compound of the present invention, 10 parts of Ethofenprox, 5 parts of Solpol, and 65 parts of Radiolite were uniformly mixed to obtain 100 parts of a mixed wettable powder containing 20% of the compound of the invention and 10% of Etofenblocks.

The insecticide of the present invention is generally applied at a rate of from 1 g to 10 kg/10 a, and preferably from 10 g to 1 kg/10 a, as reduced to an active ingredient.

The controlling effects of the insecticide according to the present invention will be demonstrated by the following Test Examples.

TEST EXAMPLE 1

Insecticidal Effect to *Spodoptera litura*

A wettable powder of the compound of the present invention shown in Table 2 below was diluted with water to a concentration of 500 ppm or 100 ppm. A piece of a cabbage leaf was soaked in the chemical solution for about 30 seconds and air-dried. The dried leaf was put on a filter paper in a dish of 9 cm in diameter.

Twenty third-instar larvae of *Spodoptera litura* were set free on the leaf, and the dish was covered and place din a thermostat at 25° C. Two days after, the mortality (%) was determined. The results obtained are shown in Table 2.

TABLE 2

| Compound | Mortality (%) | |
|---|---|---|
| No. | 500 ppm | 100 ppm |
| 11 | 100 | 70 |
| 12 | 100 | 70 |
| 15 | 80 | 60 |

TABLE 2-continued

| Compound No. | Mortality (%) 500 ppm | 100 ppm |
|---|---|---|
| 20 | 100 | 100 |
| 21 | 100 | 100 |
| 22 | 100 | 100 |
| 23 | 60 | 30 |
| 24 | 100 | 100 |
| 25 | 100 | 100 |
| 26 | 90 | 50 |
| 28 | 100 | 70 |
| 29 | 90 | 50 |
| 30 | 50 | 10 |
| 37 | 100 | 100 |
| 38 | 10 | 0 |
| 39 | 10 | 0 |
| 40 | 100 | 100 |
| 41 | 40 | 0 |
| 45 | 100 | 60 |
| 46 | 90 | 30 |
| 47 | 100 | 100 |
| 49 | 100 | 100 |
| 50 | 100 | 100 |
| 51 | 100 | 100 |
| 52 | 100 | 100 |
| 53 | 100 | 100 |
| 54 | 100 | 100 |
| 55 | 100 | 100 |
| 56 | 100 | 100 |
| 57 | 100 | 57 |
| 59 | 70 | 0 |
| 63 | 60 | 50 |
| 64 | 70 | 50 |
| 65 | 80 | 30 |
| 68 | 100 | 60 |
| 69 | 100 | 100 |
| 77 | 100 | 100 |
| 81 | 80 | 70 |
| 84 | 90 | 50 |
| 85 | 100 | 100 |
| 86 | 50 | 0 |
| 87 | 100 | 70 |
| 91 | 100 | 100 |
| 92 | 100 | 40 |
| 93 | 40 | 0 |
| 98 | 100 | 80 |
| 99 | 90 | 40 |
| 100 | 85 | 50 |

TEST EXAMPLE 2

Insecticidal Effect to *Plutella xylostella*

A wettable powder of the compound of the present invention shown in Table 3 below was diluted to a concentration of 250 ppm. The diluted solution was applied to young seedlings of white raddish of 2 to 3-leaf-stage in a pot by means of spray gun while rotating the pot on a turn-table. After air-drying, leaves were put in a plastic cup, and 20 third-instar larvae of *Plutella xyloxstella* were set free in the cup. The cup was covered and placed in a thermostat at 25° C. Four days after, the rate of death was determined. The results obtained are shown in Table 3.

TABLE 3

| Compound No. | Mortality (%) |
|---|---|
| 11 | 25 |
| 12 | 30 |
| 15 | 100 |
| 20 | 100 |
| 21 | 100 |
| 24 | 45 |
| 28 | 100 |
| 37 | 100 |
| 40 | 100 |
| 45 | 100 |

TABLE 3-continued

| Compound No. | Mortality (%) |
|---|---|
| 46 | 100 |
| 47 | 100 |
| 51 | 100 |
| 52 | 70 |
| 53 | 70 |
| 54 | 100 |
| 55 | 100 |
| 56 | 100 |
| 57 | 100 |
| 59 | 60 |
| 63 | 100 |
| 64 | 100 |
| 65 | 75 |
| 86 | 50 |
| 87 | 50 |
| 91 | 100 |
| 92 | 100 |
| 93 | 100 |

TEST EXAMPLE 3

Insecticidal Effect on *Musca domestica vicina*

The compound of the present invention shown in Table 4 below was diluted with acetone to a concentration of 100 ppm. One milliliter of the solution was dropped in a glass dish of 9 cm in diameter and air-dried.

Fifteen imaginal male *Musca domestica vicina* were set free in the dish in a thermostat at 25° C. After 24 hours, the rate of death was determined. The results obtained are shown in Table 4.

TABLE 4

| Compound No. | Mortality (%) |
|---|---|
| 12 | 41 |
| 15 | 90 |
| 20 | 80 |
| 21 | 93 |
| 22 | 100 |
| 23 | 82 |
| 24 | 80 |
| 25 | 92 |
| 26 | 87 |
| 28 | 91 |
| 29 | 97 |
| 30 | 53 |
| 37 | 88 |
| 45 | 83 |
| 47 | 70 |
| 49 | 85 |
| 54 | 100 |
| 55 | 100 |
| 56 | 83 |
| 57 | 97 |
| 58 | 37 |
| 59 | 67 |
| 63 | 87 |
| 64 | 52 |
| 65 | 81 |
| 68 | 40 |
| 69 | 92 |
| 77 | 100 |
| 81 | 97 |
| 84 | 97 |
| 85 | 91 |
| 86 | 100 |
| 87 | 83 |
| 91 | 100 |
| 92 | 100 |
| 93 | 100 |

It can be seen from the results in Tables 2 to 4 that the insecticides of the present invention having a chemical structure entirely different from those of the conventional insecticides show broad insecticidal activity particularly against noxious insects belonging to Diptera and Lepidoptera. Considering the outbreak of noxious insects resistant to chlorinated organic compounds, organophosphorus compounds, carbamate compounds, pyrethroids, and skin formation inhibitory agents, the insecticidal compositions according to the present invention are very useful for agriculture and horticulture.

While the invention has been described in detail and with reference to specific embodiments thereof, it will be apparent to one skilled in the art that various changes and modifications can be made therein without departing from the spirit and scope thereof.

What is claimed is:

1. A crotonic acid amide derivative represented by formula (I):

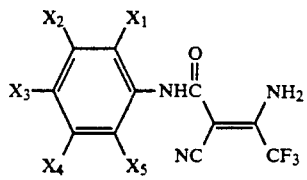

wherein $X_1$, $X_2$, $X_3$, $X_4$, and $X_5$, which may be the same or different, each represents a hydrogen atom, a halogen atom, a substituted or unsubstituted lower alkyl group, a substituted or unsubstituted lower alkoxy group, a lower haloalkyl group, a lower haloalkoxy group, a nitro group, a substituted or unsubstituted lower alkanesulfonyl group, a substituted or unsubstituted alkanesulfonyloxy group, a substituted or unsubstituted benzenesulfonyl group, a substituted or unsubstituted benzenesulfonyloxy group, a substituted or unsubstituted phenoxy group, a substituted or unsubstituted benzyloxy group, a dialkylamino group, a mono- or di-lower alkanesulfonylamino group, a substituted or unsubstituted lower alkylthio group, a $-SO_2R_1$ wherein $R_1$ represents a lower alkyl group or a lower haloalkyl group, a lower alkoxycarbonyloxy group, a substituted or unsubstituted alkoxycarbonyl group, a $-CH=N-OR_2$ group wherein $R_2$ represents a lower alkyl group, a substituted or unsubstituted pyrazolyl-1-yl group, a substituted or unsubstituted pyridyloxy group, or a pyrimidyl group; $X_2$ may be bonded to $X_1$ or $X_3$ to form a ring.

2. An insecticide composition comprising an insecticidal effective amount of a crotonic acid amine derivative represented by formula (I) below and a carrier:

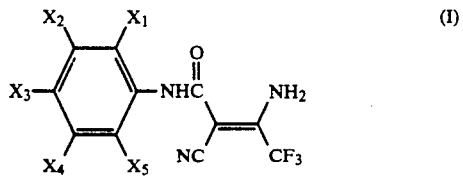

wherein $X_1$, $X_2$, $X_3$, $X_4$ and $X_5$, which may be the same or different, each represents a hydrogen atom, a halogen atom, a substituted or unsubstituted lower alkyl group, a substituted or unsubstituted lower alkoxy group, a lower haloalkyl group, a lower haloalkoxy group, a nitro group, a substituted or unsubstituted lower alkanesulfonyl group, a substituted or unsubstituted alkanesulfonyloxy group, a substituted or unsubstituted benzenesulfonyl group, a substituted or unsubstituted benzenesulfonyloxy group, a substituted or unsubstituted phenoxy group, a substituted or unsubstituted benzyloxy group, a dialkylamino group, a mono- or di-lower alkanesulfonylamino group, a substituted or unsubstituted lower alkylthio group, a $-SO_2R_1$ wherein $R_1$ represents a lower alkyl group or a lower haloalkyl group, a lower alkoxycarbonyloxy group, a substituted or unsubstituted alkoxycarbonyl group, a $-CH=N-OR_2$ group wherein $R_2$ represents a lower alkyl group, a substituted or unsubstituted pyrazolyl-1-yl group, a substituted or unsubstituted pyridyloxy group, or a pyrimidyl group; $X_2$ may be bonded to $X_1$ to $X_3$ to form a ring, as an active ingredient.

3. The insecticide composition of claim 2, wherein said carrier is selected from the group consisting of inorganic substances, organic substances of vegetable-origin, high-molecular weight compounds, urea and waxes.

4. The insecticide composition of claim 2, further comprising physiologically active substances other than said crotonic acid amide derivative.

5. The insecticide composition of claims 2 or 4, wherein the total amount of the active ingredient present is from 0.001 to 95% by weight of said composition.

* * * * *